United States Patent
Fujita et al.

(10) Patent No.: US 11,603,447 B2
(45) Date of Patent: Mar. 14, 2023

(54) METHODS FOR PRODUCING CHITIN OLIGOMER, N-ACETYLGLUCOSAMINE, AND 1-O-ALKYL-N-ACETYLGLUCOSAMINE

(71) Applicants: SHOWA DENKO K. K., Tokyo (JP); NATIONAL UNIVERSITY CORPORATION HOKKAIDO UNIVERSITY, Hokkaido (JP)

(72) Inventors: Ichiro Fujita, Tokyo (JP); Atsushi Fukuoka, Hokkaido (JP); Hirokazu Kobayashi, Hokkaido (JP)

(73) Assignees: SHOWA DENKO K. K., Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 168 days.

(21) Appl. No.: 16/096,857

(22) PCT Filed: Jan. 19, 2017

(86) PCT No.: PCT/JP2017/001740
§ 371 (c)(1),
(2) Date: Oct. 26, 2018

(87) PCT Pub. No.: WO2017/187672
PCT Pub. Date: Nov. 2, 2017

(65) Prior Publication Data
US 2019/0136008 A1 May 9, 2019

(30) Foreign Application Priority Data
Apr. 27, 2016 (JP) .............................. JP2016-089270

(51) Int. Cl.
C08J 11/24 (2006.01)
C07H 5/06 (2006.01)
C08B 37/08 (2006.01)
C08L 5/08 (2006.01)
C07B 61/00 (2006.01)

(52) U.S. Cl.
CPC ............... *C08J 11/24* (2013.01); *C07H 5/06* (2013.01); *C08B 37/003* (2013.01); *C08L 5/08* (2013.01); *C07B 61/00* (2013.01); *C08J 2305/08* (2013.01)

(58) Field of Classification Search
CPC .................................. C08J 11/24; C08B 37/03
See application file for complete search history.

(56) References Cited

U.S. PATENT DOCUMENTS

| | | | |
|---|---|---|---|
| 4,804,750 A | 2/1989 | Nishimura et al. | |
| 6,486,307 B1 * | 11/2002 | Gandhi | C08B 37/003 536/20 |

FOREIGN PATENT DOCUMENTS

| CA | 524841 A | * 5/1956 |
|---|---|---|
| EP | 0 226 452 A2 | 6/1987 |
| JP | 62-138496 A | 6/1987 |
| JP | 63-273493 A | 11/1988 |
| JP | 4-103601 A | 4/1992 |
| JP | 5-33037 A | 5/1993 |
| JP | 2001-2705 A | 1/2001 |
| JP | 2002-88093 A | 3/2002 |
| JP | 2002-177000 A | 6/2002 |
| JP | 2002-282825 A | 10/2002 |
| JP | 2003-212902 A | 7/2003 |
| JP | 2004-41035 A | 2/2004 |
| JP | 2008-253252 A | 10/2008 |
| JP | 2009-167140 A | 7/2009 |
| JP | 5426099 B2 | 2/2014 |
| KR | 20110115145 A | * 11/2011 |

OTHER PUBLICATIONS

O.C. Agboh (1986—etheses.whiterose.ac.uk "The production of fibres form chitin") (Year: 1986).*
Yabushita et al., "Catalytic Depolymerization of Chitin with Retention of N-Acetyl Group", ChemSusChem, vol. 8, pp. 3760-3763, 2015 (4 pages total).
Jyoti Agarwal et al., "Synthesis and Characterization of Monosaccharide Derivatives and Application of Sugar Based Prolinamides in Asymmetric Synthesis", European Journal of Organic Chemistry; 2012; pp. 6390-6406.
Navneet Goyal, "Synthesis and characterization of D-glucosamine-derived low molecular weight gelators", Tetrahedron, 2010, pp. 5962-5971, vol. 66.
Hirokazu Kobayashi et al., "Catalytic Depolymerization of Chitin with Retention of Acetyl Group", Shokubai Toronkai Toronkai A Yokoshu, Sep. 2016, 3 pgs., vol. 118.
Naohisa Kochibe et al., "Purification and Properties of an N-Acetylglucosamine-specific Lectin from Psathyrella velutina Mushroom", The Journal of Biological Chemistry; Jan. 5, 1989, pp. 173-177, vol. 264, No. 1.
Fereidoon Shahidi et al., "Food Applications of chitin and chitosans", Trends in Food Science & Technology, 1999, p. 37-51; vol. 10.
T.V. Rajanbabu et al., "Carbohydrate Phosphinites as Practical Ligands in Asymmetric Catalysis: Electronic Effects and Dependence of Backbone Chirality in Rh-Catalyzed Asymmetric Hydrogenations. Synthesis of R- or S-Amino Acids Using Natural Sugars as Ligand Precursors", Journal of Organic Chemistry, 1997, pp. 6012-6028, vol. 62, No. 17.

(Continued)

Primary Examiner — Shaojia A Jiang
Assistant Examiner — Everett White
(74) Attorney, Agent, or Firm — Sughrue Mion, PLLC

(57) ABSTRACT

The present invention relates to a method of producing a chitin oligomer, including subjecting chitin-containing biomass to partial hydrolysis while pulverizing the chitin-containing biomass with a pulverization apparatus in the co-presence of water and an acid catalyst selected from phosphoric acid, nitrous acid, and an organic acid (Method 1); a method of producing N-acetylglucosamine, including hydrolyzing a chitin oligomer obtained by the Method 1 by adding water thereto, followed by heating (Method 2); and a method of producing a 1-O-alkyl-N-acetylglucosamine, including alcoholyzing a chitin oligomer by adding an alcohol thereto (Method 3).

16 Claims, 2 Drawing Sheets

(56) References Cited

OTHER PUBLICATIONS

Florence Tabary et al., "Isolation, Molecular and Biological Properties of a Lectin from Rice Embryo: Relationship with Wheat Germ Agglutinin Properties", Archives of Biochemistry and Biophysics, Nov. 15, 1987, pp. 79-88, vol. 259, No. 1.
International Search Report for PCT/JP2017/001740 dated, Mar. 14, 2017 (PCT/ISA/210).
Song, "Green Production Process for Fine Chemical Engineering", 1st ed., Guangdong Science and Technology Press, Mar. 2006, pp. 192-193 (7 pages total).
Extended European Search Report dated Nov. 22, 2019, issued by the European Patent Office in corresponding application No. 17788962.3.

* cited by examiner

METHODS FOR PRODUCING CHITIN OLIGOMER, N-ACETYLGLUCOSAMINE, AND 1-O-ALKYL-N-ACETYLGLUCOSAMINE

CROSS REFERENCE TO RELATED APPLICATIONS

This application is a National Stage of International Application No. PCT/JP2017/001740 filed Jan. 19, 2017, claiming priority based on Japanese Patent Application No. 2016-089270, filed Apr. 27, 2016.

TECHNICAL FIELD

The present invention relates to methods of producing a chitin oligomer, N-acetylglucosamine (NAG), and a 1-O-alkyl-N-acetylglucosamine from chitin-containing biomass through a hydrolysis reaction of chitin using a catalyst having a low environmental load and a low risk on handling.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

REFERENCE TO A "SEQUENCE LISTING"

Not Applicable

STATEMENT REGARDING PRIOR DISCLOSURES BY THE INVENTOR OR A JOINT INVENTOR

Not Applicable

BACKGROUND OF THE INVENTION

Chitin is a nitrogen-containing polysaccharide polymer containing a β-1,4-glycosidic bond formed by NAG, and is naturally abundant as biomass contained in crustaceans, such as shrimps and crabs, insects, and fungi, such as mushrooms.

Some of solvolysis products, such as hydrolysis products and alcoholysis products, of chitin have various effects and potencies, and hence can be utilized as various functional materials.

For example, a chitin oligomer, which is a hydrolysis product, and in which two to about seven NAG molecules are polymerized, is an ingredient useful as a precursor for obtaining NAG. In addition, the chitin oligomer has been reported to have antitumor, immunostimulating, and antimicrobial actions (Trend Food Sci. Technol., 1999, 10, 37-51; Non Patent Literature 1), an intestinal environment-adjusting action through growth of bifidobacteria, and elicitor activity, which is a plant biological defense mechanism-activating action. Accordingly, the chitin oligomer is receiving attention as a pharmaceutical material, a functional food, and an agricultural material as well. In particular, research in recent years has found that the chitin oligomer has elicitor activity, which is a plant biological defense mechanism-activating action, and its utilization as an agricultural material has been desired. However, when a sulfate radical or the like remains in the hydrolysis product, the hydrolysis product needs to be purified in order to serve as an agricultural material. Accordingly, there is a demand for a material exhibiting no adverse effect even when sprayed to arable land over a long period of time.

In addition, NAG, which is a monomer of the hydrolysis product, is an ingredient that, when taken up by a body, promotes biosynthesis of mucopolysaccharides, such as hyaluronic acid, to thereby exhibit effects, such as a knee/joint pain-ameliorating effect and a skin-beautifying/moisturizing effect. NAG is less bitter and has higher utilization efficiency than glucosamine, which shows similar effects. Therefore, in recent years, NAG has been expected to be utilized as a functional food, a pharmaceutical-related raw material, and a cosmetic-related raw material.

Further, 1-O-methyl-N-acetylglucosamine (hereinafter sometimes abbreviated as "MeNAG"), which is a methanolysis product and is an NAG derivative, has suppressive effects on influenza and cancer through inhibition of hemagglutination. Accordingly, the substance is receiving attention as a raw material for a pharmaceutical product (Arch. Biochem. Biophys., 1987, 259, 79-88; Non Patent Literature 2, J. Biol. Chem., 1989, 264, 173-177; Non Patent Literature 3), and has been shown to have potential to have its applications expanded to an organic catalyst (Eur. J. Org. Chem., 2012, 6390-6406; Non Patent Literature 4), a ligand (J. Org. Chem., 1997, 62, 6012-6028; Non Patent Literature 5), a gelator (Tetrahedron, 2010, 66, 5962-5971; Non Patent Literature 6), and the like.

As a method of producing the chitin oligomer or NAG from chitin involving using an acid, there have been developed methods each involving subjecting chitin to partial hydrolysis through a reaction using concentrated hydrochloric acid under a heating condition of around 40° C. for from 3 hours to 4 hours to produce an oligomer, followed by a subsequent step (JP 05-33037 B2; Patent Literature 1, JP 2009-167140 A; Patent Literature 2, JP 5426099 B2; Patent Literature 3). In each of Patent Literatures 1 and 2, NAG is produced by introducing an enzymatic reaction as the subsequent step, and in Patent Literature 3, NAG is produced by introducing cooling crystallization as the subsequent step. However, in each of those methods, a ratio of the number of moles of an N-acetylglucosamine unit ($C_8H_{13}NO_5$) in chitin serving as a substrate to the number of moles of an acid catalyst (hereinafter abbreviated as "S/C ratio") is from 0.08 to 0.14. That is, a large amount of concentrated hydrochloric acid is used with respect to the substrate. Moreover, each of the methods has a problem in that a yield of the produced oligomer or NAG with respect to chitin is low. In addition, for another acid, there has also been developed a method involving performing treatment with sulfuric acid at from 0° C. to 50° C. for from 5 minutes to 2 hours (JP 2002-88093 A; Patent Literature 4). However, also in this method, the S/C is from 0.05 to 0.5. That is, a large amount of sulfuric acid is used.

As described above, each of the hitherto developed production methods involving using an acid uses a large amount of a strong acid that is difficult to handle, and hence has problems of imposing an environmental load and being costly.

Meanwhile, there have been proposed methods each involving utilizing microorganisms having a chitinase-producing ability for chitin without using an acid (JP 2004-41035 A; Patent Literature 5, JP 2008-253252 A; Patent Literature 6). However, each of those methods takes a long period time of from 4 days to 5 days and also has low chitin-decomposing efficiency, and hence has a problem of low productivity.

In addition, as described in Patent Literatures 1 to 3, MeNAG has been produced by a methanolysis method involving adding methanol to a chitin oligomer prepared by subjecting chitin to partial hydrolysis with hydrochloric acid, and heating the mixture. However, also in this case, there is a problem in that a large amount of the acid is used.

Under the above-mentioned circumstances, it is desired to establish efficient methods of producing a chitin oligomer, N-acetylglucosamine, and a 1-O-alkyl-N-acetylglucosamine, each involving using an acid that is easy to handle in a small use amount with a low environmental load.

CITATION LIST

Patent Literature

[PTL 1] JP 05-33037 B2
[PTL 2] JP 2009-167140 A
[PTL 3] JP 5426099 B2
[PTL 4] JP 2002-88093 A
[PTL 5] JP 2004-41035 A
[PTL 6] JP 2008-253252 A

Non Patent Literature

[NPL 1] Trend Food Sci. Technol., 1999, 10, 37-51
[NPL 2] Arch. Biochem. Biophys., 1987, 259, 79-88
[NPL 3] J. Biol. Chem., 1989, 264, 173-177
[NPL 4] Eur. J. Org. Chem., 2012, 6390-6406
[NPL 5] J. Org. Chem., 1997, 62, 6012-6028
[NPL 6] Tetrahedron, 2010, 66, 5962-5971

BRIEF SUMMARY OF THE INVENTION

Technical Problem

An object of the present invention is to provide methods of producing a chitin oligomer, N-acetylglucosamine, and a 1-O-alkyl-N-acetylglucosamine through a hydrolysis reaction of chitin-containing biomass using an acid catalyst that is easy to handle in a small amount as compared to related-art methods.

Solution to Problem

The inventors of the present invention have found that a chitin oligomer can be produced through partial hydrolysis in a hydrolysis reaction of chitin-containing biomass with an acid catalyst by physically pulverizing the chitin-containing biomass in the presence of water using an acid having a low risk on handling as the acid catalyst is in a small amount as compared to related-art methods. The inventors have also found that N-acetylglucosamine can be produced by hydrolyzing the chitin oligomer by adding water thereto, followed by heating, and that a 1-O-alkyl-N-acetylglucosamine can be produced by alcoholyzing the chitin oligomer by adding an alcohol thereto, followed by heating. Thus, the inventors have completed the present invention.

That is, the present invention relates to a method of producing a chitin oligomer according to the following items [1] to [9], a method of producing N-acetylglucosamine according to the following items [10] and [11], and a method of producing a 1-O-alkyl-N-acetylglucosamine according to the following items [12] to [15].

[1] A method of producing a chitin oligomer, including subjecting chitin-containing biomass to partial hydrolysis while pulverizing the chitin-containing biomass with a pulverization apparatus in the co-presence of water and an acid catalyst selected from phosphoric acid, nitrous acid, and an organic acid.

[2] The method of producing a chitin oligomer according to 1 above, wherein the acid catalyst is phosphoric acid.

[3] The method of producing a chitin oligomer according to 2 above, wherein a ratio (S/C) of a number of moles (S) of an N-acetylglucosamine unit ($C_8H_{13}NO_5$) in chitin to a number of moles (C) of the acid catalyst is from 0.2 to 20.

[4] The method of producing a chitin oligomer according to any one of 1 to 3 above, wherein the pulverizing includes pulverizing the chitin-containing biomass, which is impregnated with the acid catalyst in advance, in the presence of water.

[5] The method of producing a chitin oligomer according to 4 above, wherein the method includes mixing a solvent having dissolved therein the acid catalyst with the chitin-containing biomass, then removing the solvent to impregnate the chitin-containing biomass with the acid catalyst, and pulverizing the resultant chitin-containing biomass impregnated with the acid catalyst in the presence of water.

[6] The method of producing a chitin oligomer according to 5 above, wherein the solvent is free of modifying the chitin-containing biomass, free of inhibiting acid catalyst activity, and capable of being removed by heating or distillation.

[7] The method of producing a chitin oligomer according to 6 above, wherein the solvent is selected from water, diethyl ether, hexane, and benzene.

[8] The method of producing a chitin oligomer according to any one of 1 to 7 above, wherein the pulverization apparatus is a ball mill.

[9] The method of producing a chitin oligomer according to 8 above, wherein the ball mill is a planetary ball mill or a tumbling ball mill.

[10] A method of producing N-acetylglucosamine, including hydrolyzing a chitin oligomer obtained by the method of any one of 1 to 9 above by adding water thereto, followed by heating.

[11] The method of producing N-acetylglucosamine according to 10 above, wherein the heating is performed at a temperature of from 100° C. to 260° C.

[12] A method of producing a 1-O-alkyl-N-acetylglucosamine, including alcoholyzing a chitin oligomer obtained by the method of any one of 1 to 9 above by adding an alcohol thereto.

[13] The method of producing a 1-O-alkyl-N-acetylglucosamine according to 12 above, wherein the alcohol is a monohydric alcohol.

[14] The method of producing a 1-O-alkyl-N-acetylglucosamine according to 12 or 13 above, wherein the alcohol is methanol, and wherein the 1-O-alkyl-N-acetylglucosamine is 1-O-methyl-N-acetylglucosamine.

[15] The method of producing a 1-O-alkyl-N-acetylglucosamine according to any one of 12 to 14 above, wherein the alcoholysis is performed under heating at a temperature of from 120° C. to 280° C.

Advantageous Effects of Invention

According to the present invention, the chitin oligomer, N-acetylglucosamine, and the 1-O-alkyl-N-acetylglucosamine can be produced from chitin-containing biomass at low cost using an acid catalyst having a low environmental load.

DETAILED DESCRIPTION OF THE INVENTION

Figure 1:
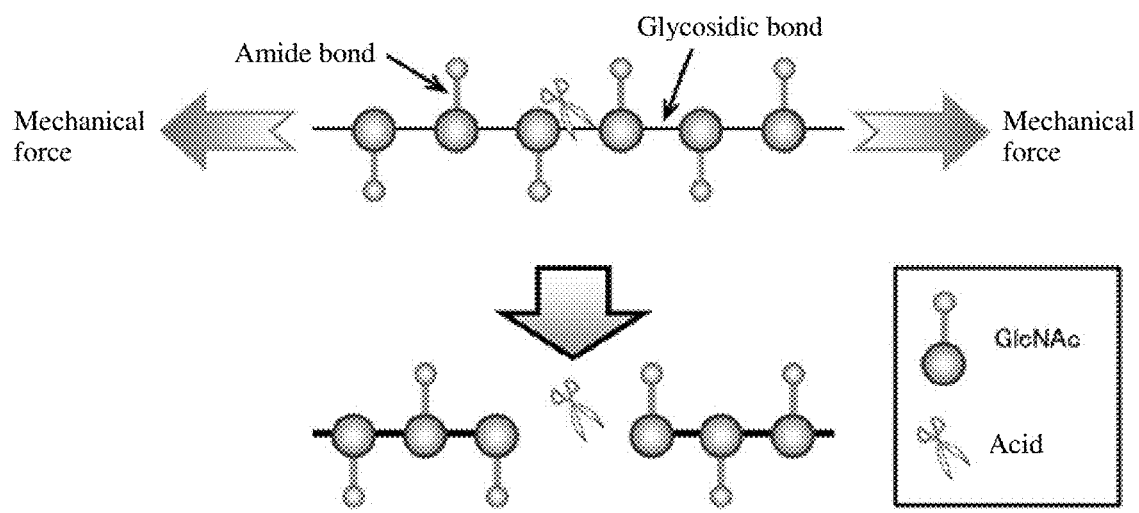
FIG. 1 is a diagram for illustrating the cleavage of only a glycosidic bond of chitin by virtue of a synergistic effect of an acid catalyst and a physical force.

Now, embodiments of the methods according to the present invention are described. The embodiments to be described below are illustrative of typical examples of the present invention, and the present invention is not limited thereto.

Chitin-Containing Biomass (Solid Substrate):

The term "biomass" generally refers to a "recyclable organic resource of biological origin, excluding fossil resources," but "chitin-containing biomass" (hereinafter sometimes referred to as "solid substrate") to be used in the present invention is, for example, biomass mainly containing chitin, such as the shell or cuticle of a crustacean, such as a shrimp or a crab, an arthropod, an insect, a squid, a shellfish, krill, or the like, or the cell wall of a fungus, such as a mushroom.

The chitin-containing biomass may be used after being subjected to purification treatment, or without being subjected to purification treatment. An example of the chitin-containing biomass subjected to purification treatment is biomass that has been subjected to treatments, such as the dissolution of protein with an alkali and the dissolution of calcium with an acid, and then subjected to treatments, such as neutralization, solid-liquid separation, and water washing, to remove impurities, such as protein and calcium, and that contains chitin. Further, industrially prepared chitin or the like may also be used.

The chitin-containing biomass may contain, as the impurities, protein, phosphoric acid, iron, copper, zinc, molybdenum, silicon, aluminum, calcium, magnesium, potassium, sodium, and the like each derived from a raw material.

The form of the chitin-containing biomass may be dry or wet, and may be crystalline or non-crystalline. The chitin-containing biomass is desirably subjected to rough pulverization prior to a reaction. The rough pulverization increases the ease of contact with a catalyst to promote a hydrolysis reaction. Therefore, the chitin-containing biomass preferably has a shape and size suited for pulverization. An example of such shape and size is a powder form having a particle diameter of from 20 μm to 1,000 μm.

The rough pulverization treatment may be performed with, for example: a rough pulverizer, such as a shredder, a jaw crusher, a gyratory crusher, a cone crusher, a hammer crusher, a roll crusher, or a roll mill; or a medium pulverizer, such as a stamp mill, an edge runner, a cutting/shearing mill, a rod mill, an autogenous mill, or a roller mill. A pulverization treatment time is not particularly limited as long as the raw material is uniformly and finely powdered as a result of the treatment.

Acid Catalyst:

An acid catalyst to be used in the present invention is not particularly limited as long as the catalyst allows chitin to be hydrolyzed, and for example, a catalyst having activity of hydrolyzing a β-1,4-glycosidic bond forming a main chain of chitin serving as a main component is preferred.

Phosphoric acid and/or an organic acid is preferably used as the acid catalyst from the viewpoints of an environmental load and safety on handling, and for example, an inorganic acid, such as phosphoric acid or nitrous acid, or an organic acid, such as formic acid, acetic acid, oxalic acid, propionic acid, citric acid, or succinic acid, may be used. In addition, those acid catalysts may be used in combination thereof. Further, phosphoric acid, acetic acid, citric acid, or nitrous acid is more preferred from the viewpoints of allowing the rate of the hydrolysis of the chitin-containing biomass with the acid catalyst to be increased, and being usable as an agricultural material together with a decomposition product, and phosphoric acid, which serves as a nutrient source for a plant, is most preferred.

Figure 3:
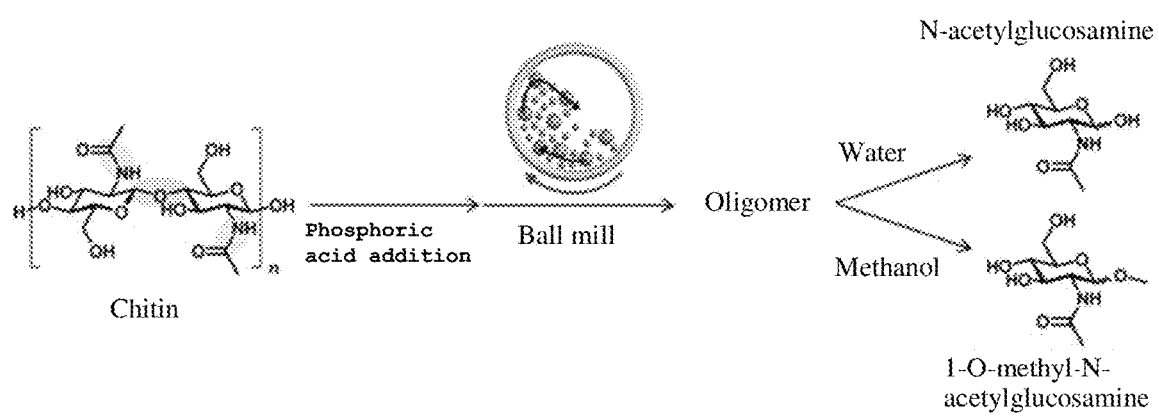
FIG. 3 is a scheme for the synthesis of a chitin oligomer, N-acetylglucosamine, and a 1-O-alkyl-N-acetylglucosamine from chitin according to the present invention.

As illustrated in a scheme of FIG. 3, the present invention includes: a method of producing a chitin oligomer by subjecting chitin in the solid substrate to partial hydrolysis (method 1); a method of producing N-acetylglucosamine by subjecting a chitin oligomer produced by the method 1 to hydrolysis in water (method 2); and a method of producing a 1-O-alkyl-N-acetylglucosamine by subjecting a chitin oligomer produced by the method 1 to alcoholysis in an alcohol solvent (method 3). Each of the methods is described below.

Method 1 (Partial Hydrolysis Reaction):

The partial hydrolysis of the solid substrate is performed by impregnating the substrate with the acid catalyst, and then applying a mechanical stress by pulverization. The term "partial hydrolysis" refers to a hydrolysis reaction in which most of the depolymerization products of chitin proceed no further than water-soluble oligomer units and depolymerization hardly reaches a monomer unit.

Chitin has two bonds subject to hydrolysis, i.e., a β-1,4-glycosidic bond forming a polymer main chain of NAG, and an amide bond of an acetamido group (—NHCOCH$_3$) forming a side chain at a C2 position. However, the target compounds of the present invention each have the acetamido group in the side chain, and hence it is important that the β-1,4-glycosidic bond of the main chain be selectively hydrolyzed.

A ratio between the acid catalyst (C) and the solid substrate (S) is not particularly limited, but from the viewpoints of partial hydrolysis efficiency at the time of the reaction and substrate residue reduction after the reaction, a molar ratio S/C may be set to from 0.2 to 20, preferably from 0.5 to 15, more preferably from 1 to 10.

A method for the impregnation of the solid substrate with the acid catalyst may be direct mixing of the solid substrate and the acid catalyst. Alternatively, after mixing of a solvent having dissolved therein the acid catalyst with the substrate, the solvent may be removed by distillation or heating. The solvent to be used is not particularly limited as long as the solvent is free of modifying the substrate, is free of inhibiting or deactivating acid catalyst activity, and is not non-volatile (i.e., is capable of being removed by heating or distillation). For example, water, diethyl ether, hexane, benzene, or the like is appropriate.

With regard to water at the time of the partial hydrolysis, when the solid substrate impregnated with the acid catalyst has physisorbed thereto about 1 mass % to about 3 mass % of water, the partial hydrolysis can be sufficiently provided for. Accordingly, in general, water may not be added without any problem. However, water may be added.

The partial hydrolysis can be achieved by pulverizing the solid substrate impregnated with the acid catalyst. In this case, possible effects of fine powderization of the solid substrate by the pulverization are as follows: the acid catalyst with which the solid substrate is impregnated is more uniformly diffused and increased in specific surface area, leading to an improvement in transmission efficiency of a physical stress; and chitin is amorphized to improve the hydrolyzability of the solid substrate.

As an apparatus to be used for the pulverization treatment, there are given: tumbling ball mills, such as a pot mill, a tube mill, and a conical mill; jet pulverizers, such as a spiral flow jet mill, a collision type jet mill, a fluidized bed type jet mill, and a wet type jet mill; shear mills, such as a Raikai mixer and an angmill; colloid mills, such as a mortar and a stone mill; impact type pulverizers, such as a hammer mill, a cage mill, a pin mill, a disintegrator, a screen mill, a turbo mill, and a centrifugal classification mill; a planetary ball mill, which is a pulverizer of a type that employs rotation and revolution movements; and the like.

From the viewpoint of achieving the purpose of the present invention, i.e., selective hydrolysis of the glycosidic bond of the main chain, the pulverization apparatus to be used is preferably a ball mill, in which a compressive force is strongly applied to the solid substrate and tensile stresses are applied in both directions of the main chain, more preferably a planetary ball mill or a tumbling ball mill, most preferably a planetary ball mill.

A temperature at which the pulverization treatment is performed is not particularly limited as long as the β-1,4-glycosidic bond in the main chain can be selectively hydrolyzed without the elimination of the acetamido group in the side chain, but the temperature is preferably from ordinary temperature to 100° C., more preferably from 45° C. to 90° C., still more preferably from 60° C. to 80° C.

A period of time for which the pulverization treatment is performed is not particularly limited as long as the solid substrate undergoes the partial hydrolysis to such a degree as to become water-soluble. In order to determine the end point of the treatment, it is preferred that the water solubilities of samples acquired over time be confirmed.

The reaction product obtained by the partial hydrolysis (method 1) may be then used as a raw material for each of the method 2 involving performing hydrolysis and the method 3 involving performing alcoholysis, which are described later, and may also be used as a chitin oligomer by being subjected to purification treatments, such as neutralization and desalting.

Method 2 (Hydrolysis Reaction) and Method 3 (Alcoholysis Reaction):

In each of the hydrolysis reaction of the method 2 and the alcoholysis reaction of the method 3, the reaction product obtained by the partial hydrolysis of the method 1 may be used as a raw material. In actuality, the raw material is dissolved in a solvent (water or an alcohol), and then the solution is heated to be subjected to a reaction. In the method 2, water is used as the solvent, and NAG is produced from the chitin oligomer. In the method 3, an alcohol is used as the solvent, and a 1-O-alkyl-N-acetylglucosamine, which is an NAG derivative, is produced from the chitin oligomer.

The solvent to be used in the method 3 is preferably a monohydric alcohol, such as methanol, ethanol, 1-propanol, 2-propanol, 1-butanol, 2-butanol, 2-methyl-1-propanol, or 2-methyl-2-propanol. From the viewpoint of obtaining efficiency and uniformity of the reaction by dissolving the raw material, the solvent is more preferably methanol or ethanol, most preferably methanol.

The reaction is generally performed in the presence of the raw material and the solvent in a sealed vessel at ordinary pressure. For example, when the solvent is water, the reaction is performed at a temperature at which a pressurized state having a water vapor partial pressure of 0.1 MPa or more is achieved. In the hydrolysis reaction of the method 2, the heating temperature at which the pressurized state is achieved is preferably from 100° C. to 260° C., more preferably from 130° C. to 230° C., still more preferably from 150° C. to 210° C. In addition, in the alcoholysis reaction of the method 3, the heating temperature is preferably from 120° C. to 280° C., more preferably from 150° C. to 250° C., still more preferably from 170° C. to 230° C. The heating temperature is the temperature of the solution during the reaction. When the heating temperature is set to fall within the range, the production yield of the target product can be increased. The reaction in the production method of the present invention is generally performed in a sealed vessel, such as an autoclave, and hence, even when the heating is started at ordinary pressure, the reaction system is brought into a pressurized state by the heating at the above-mentioned temperature.

Further, the reaction may also be performed with the inside of the sealed vessel being pressurized before the reaction or during the reaction. The inside of the sealed vessel is pressurized to a pressure of, for example, from 0.1 MPa to 30 MPa, preferably from 1 MPa to 20 MPa, more preferably from 2 MPa to 10 MPa.

In the heating in the reaction, a period of time in which the temperature reaches the reaction temperature from room temperature is preferably from 5 minutes to 60 minutes, more preferably from 5 minutes to 30 minutes, still more preferably from 5 minutes to 20 minutes. It is preferred that, at the same time when the reaction temperature is reached, the heating be stopped to allow cooling. With this, the production yield of NAG can be increased.

The amount of water to be used for the decomposition (mass ratio with respect to 1 part by mass of the raw material) is at least an amount allowing the whole amount of the chitin oligomer in the biomass to be solvolyzed. In consideration of, for example, the fluidity and stirring property of the reaction mixture, the amount of water is preferably from 1 part by mass to 500 parts by mass, more preferably from 2 parts by mass to 350 parts by mass, still more preferably from 2 parts by mass to 200 parts by mass. When the amount of water is set to fall within the range, a high product yield and a high product concentration can both be achieved in the decomposition reaction.

The reaction is preferably performed while the reaction mixture is stirred. The reaction may be performed in any mode, such as a batch mode or a continuous mode.

EXAMPLES

Now, the present invention is described in more detail by way of Examples and Comparative Examples. However, the present invention is by no means limited to the descriptions thereof.

[Raw Material Used]

A crab shell was dried, pulverized, and immersed in a dilute sodium hydroxide aqueous solution at high temperature and a dilute hydrochloric acid aqueous solution at room temperature for several hours each to remove protein and calcium carbonate. The thus purified chitin was used.

[Partial Hydrolysis Reaction of Chitin (Method 1)]

Comparative Example 1: Untreated Chitin

The purified chitin (average particle diameter: 73 μm) was used as it was. This sample is referred to as untreated chitin.

Comparative Example 2: Phosphoric Acid-Impregnated Chitin 1

10 g of the untreated chitin (average particle diameter: 73 μm) (49.2 mmol in terms of NAG unit) was dispersed in 30 mL of water containing 2.4 g of phosphoric acid (24.6 mmol, S/C ratio: 2.0), and then the dispersion was dried under reduced pressure to provide powder having a water content of 2.5 mass %. This sample is referred to as phosphoric acid-impregnated chitin 1.

Comparative Example 3: Phosphoric Acid-Impregnated Chitin 2

10 g of the untreated chitin (average particle diameter: 73 μm) (49.2 mmol in terms of NAG unit) was dispersed in 30 mL of water containing phosphoric acid in an amount of 4.8 g (49.2 mmol, S/C ratio: 1.0), and then the dispersion was dried under reduced pressure to provide powder having a water content of 4.5 mass %. This sample is referred to as phosphoric acid-impregnated chitin 2.

Comparative Example 4: Chitin Pulverized Product 5.0 g of the untreated chitin (average particle diameter: 73 μm) was placed in an alumina pot having a volume of 250 mL together with 100 g of alumina balls each having a diameter of 5 mm. The pot was set in a planetary ball mill (manufactured by Fritsch, PULVERISETTE (trademark) 6), and treatment was performed at 500 rpm for a continuous 6 hours. As a result, powder containing 4.2 mass % of physisorbed water was obtained. This sample is referred to as chitin pulverized product (average particle diameter: 42 μm).

Example 1: Phosphoric Acid-impregnated Chitin Pulverized Product 1

5 g of phosphoric acid-impregnated chitin 1 was placed into an alumina pot having a volume of 250 mL together with 100 g of alumina balls each having a diameter of 5 mm. This pot was set in a planetary ball mill (manufactured by Fritsch, PULVERISETTE 6), and treatment was performed at 500 rpm for a continuous 6 hours. As a result, powder containing 3.1 mass % of physisorbed water was obtained. This sample is referred to as phosphoric acid-impregnated chitin pulverized product 1.

Example 2: Phosphoric Acid-impregnated Chitin Pulverized Product 2

5 g of phosphoric acid-impregnated chitin 2 was placed into an alumina pot having a volume of 250 mL together with 100 g of alumina balls each having a diameter of 5 mm. This pot was set in a planetary ball mill (Fritsch, PULVERISETTE 6), and treatment was performed at 500 rpm for a continuous 6 hours. As a result, powder containing 5.3 mass % of physisorbed water was obtained. This sample is referred to as phosphoric acid-impregnated chitin pulverized product 2.

Comparative Example 5: Sulfuric Acid-Impregnated Chitin Pulverized Product 10.0 g of chitin (average particle diameter: 73 μm) (49.2 mmol in terms of NAG unit) was dispersed in 30 mL of water containing 2.4 g of sulfuric acid (24.6 mmol, S/C ratio: 2.0), and then the dispersion was dried under reduced pressure. 5 g of the thus obtained powder was taken and placed in an alumina pot having a volume of 250 mL together with 100 g of alumina balls each having a diameter of 5 mm. This pot was set in a planetary ball mill (Fritsch, PULVERISETTE 6), and treatment was performed at 500 rpm for a continuous 6 hours. As a result, powder containing 3.1 mass % of physisorbed water was obtained. This sample is referred to as sulfuric acid-impregnated chitin pulverized product.

[Solubility Measurement of Partial Hydrolysis Reaction Sample of Chitin]

100 mg of each of the samples of Examples 1 and 2, and Comparative Examples 1 to 5 was weighed, and added to 50 mL of distilled water. The mixture was shaken, and then subjected to ultrasonic treatment for 10 minutes to dissolve soluble matter. The series of treatments was performed at a temperature of 25° C., and the resultant suspension was filtered through a 0.1 μm filter of polytetrafluoroethylene (PTFE). The solid residue was further washed by filtration with 5 mL of distilled water, and placed in an oven at 110° C. and dried overnight. The mass of the resultant was measured, and a solubilization ratio was calculated by the following equation.

Solubility ratio (%)={(mass of weighed sample-dry mass of recovered solid content)/mass of weighed sample}×100

The measurement results of the solubility are shown in Table 1. The untreated chitin (Comparative Example 1) had a solubility of 0%, showing no solubility. Even among the treated samples, the phosphoric acid-impregnated chitin 1 (Comparative Example 2) and the phosphoric acid-impregnated chitin 2 (Comparative Example 3), which were subjected to only the acid addition, had solubilities of 1.2% and 4.4%, respectively, and the chitin pulverized product sample (Comparative Example 4), which was subjected to only the ball mill pulverization, had a solubility of 5.2%, each showing only a significantly low solubility.

Meanwhile, the phosphoric acid-impregnated chitin pulverized products (Examples 1 and 2) and the sulfuric acid-impregnated chitin pulverized product (Comparative Example 5) each obtained by subjecting acid-impregnated chitin to the ball mill pulverization in the presence of an acid were mostly dissolved, each showing a solubility of 99%.

It was confirmed from those results that, although hardly any chitin-solubilizing effect was obtained by a single treatment, i.e., the acid catalyst addition or the planetary ball mill pulverization, a remarkable synergistic effect was obtained by performing pulverization treatment for applying a mechanical stress in the presence of an acid, and significantly promoted the solubilization of chitin.

Further, it was confirmed that chitin was solubilized by the planetary ball mill even when phosphoric acid serving as a weak acid having a lower risk than a strong acid and a low environmental load was used in place of sulfuric acid serving as a strong acid.

The solubilization ratio and the total yield of the products were reversed in each of Comparative Example 2 and Comparative Example 3 probably because phosphoric acid supported on chitin was not completely removed by washing and the apparent solubilization ratio was reduced.

[Acetic Acid Measurement of Aqueous Suspension Filtrate of Partial Hydrolysis Reaction Sample of Chitin]

An aqueous suspension filtrate of each of the samples of Examples 1 and 2, and Comparative Examples 1 to 5 was quantitatively analyzed for acetic acid with a high performance liquid chromatograph (apparatus: LC-10ATVP manufactured by Shimadzu Corporation, column: Phenomenex (trademark) Synergi 4 μm Hydro-RP 80 Å φ0.6×250 mm, mobile phase: 40 mM potassium phosphate buffer, pH 2.9, 0.8 mL/min, 30° C., detection: differential refractive index). As a result, acetic acid was not detected in any of the samples.

Thus, it was suggested that, in the partial hydrolysis of chitin by the ball mill pulverization in the co-presence of an acid catalyst, the amide bond of the acetamido group (—NHCOCH$_3$) at the C2 position of each of NAG units constituting chitin was maintained and the glycosidic bond linking the NAG units to each other was selectively cleaved. This is presumably because, in a system in which hydrolysis is facilitated in the co-presence of a small amount of the acid catalyst, a mechanical stress applied by the ball mill pulverization exhibits an action of squeezing chitin to extend the chitin in both directions of polymerization, that is, an action of pulling the glycosidic bond forming the main chain, to thereby provide a synergistic effect of accelerating the selective hydrolysis of the glycosidic bond, which has not been obtained in related-art hydrolysis performed by acid addition alone (see FIG. 1).

[HPLC Analysis of Aqueous Suspension Filtrate of Partial Hydrolysis Reaction Sample of Chitin]

An aqueous suspension filtrate of each of the samples of Examples 1 and 2, and Comparative Examples 2 to 5 was analyzed with a high performance liquid chromatograph (HPLC) (apparatus: LC-10ATVP manufactured by Shimadzu Corporation, column: Phenomenex Rezex RPM-Monosaccharide Pb++ φ7.8×300 mm, mobile phase: water, 0.6 mL/min, 70° C., detection: differential refractive index), and the yields of NAG and an oligosaccharide (degree of polymerization: 2 to 8) were calculated by the following equation.

Yield (%)={number of moles of NAG unit in product)/(number of moles of NAG unit in added raw material)}×100

The results are shown in Table 1. The phosphoric acid-impregnated chitin 1 (Comparative Example 2) subjected to only the acid addition had an NAG yield of 0.7% and an oligosaccharide yield of 1.4%, the phosphoric acid-impregnated chitin 2 (Comparative Example 3) subjected to only the acid addition had an NAG yield of 2.6% and an oligosaccharide yield of 3.9%, and the chitin pulverized product sample (Comparative Example 4) subjected to only the ball mill pulverization had an NAG yield of 0.1% and an oligosaccharide yield of 1.3%, each providing only significantly low yields.

Meanwhile, the samples subjected to the ball mill pulverization in the presence of an acid showed high oligomer yields. Specifically, the phosphoric acid-impregnated pulverized chitin 1 (Example 1) had an NAG yield of 3.3% and an oligosaccharide yield of 70%, the phosphoric acid-impregnated chitin 2 (Example 2) had an NAG yield of 5.1% and an oligosaccharide yield of 61%, and the sulfuric acid-impregnated pulverized chitin (Comparative Example 5) had an NAG yield of 10.0% and an oligosaccharide yield of 60%. It was able to be confirmed from the results that the chitin oligomer was obtained in a good yield by pulverizing the acid-impregnated chitin irrespective of which of phosphoric acid or sulfuric acid was used. In addition, the obtained chitin oligomer is a substance reported to have a plant biological defense mechanism-activating action and expected to find use as an agricultural material. When the use as an agricultural material is taken into consideration, spraying of the chitin oligomer produced using sulfuric acid for a long period of time has a risk of soil acidification due to the accumulation of sulfate radicals, and hence a purification step is needed. Meanwhile, the chitin oligomer produced using phosphoric acid may be able to be sprayed to a farm or the like without purification because a phosphate radical contained therein is utilized as a nutrient source for a plant, and hence it may be said that its economic advantage is also great.

TABLE 1

| | | Treatment conditions | | Results | | | |
|---|---|---|---|---|---|---|---|
| | Sample name (treatment procedure) | | S/C[a] | Solubilization ratio (%) | NAG yield (%) | Oligomer yield (%) | Suitability as agricultural spray |
| Example 1 | Phosphoric acid-impregnated chitin pulverized product 1 (chitin pulverized with addition of acid) | | 2.0 | 99 | 3.3 | 70 | ○ |
| Example 2 | Phosphoric acid-impregnated chitin pulverized product 2 (chitin pulverized with addition of acid) | | 1.0 | 99 | 5.1 | 61 | ○ |
| Comparative Example 1 | Untreated chitin (untreated) | | —[b] | 0 | 0.0 | 0 | x (No active ingredient) |
| Comparative Example 2 | Phosphoric acid-impregnated chitin 1 (acid-impregnated chitin) | | 2.0 | 1.2[c] | 0.7 | 1.4 | x (Minute amount of active ingredient) |
| Comparative Example 3 | Phosphoric acid-impregnated chitin 2 (acid-impregnated chitin) | | 1.0 | 4.4[c] | 2.6 | 3.9 | x (Minute amount of active ingredient) |

TABLE 1-continued

| | Treatment conditions | | Results | | | |
|---|---|---|---|---|---|---|
| | Sample name (treatment procedure) | S/C[a] | Solubilization ratio (%) | NAG yield (%) | Oligomer yield (%) | Suitability as agricultural spray |
| Comparative Example 4 | Chitin pulverized product (chitin pulverized without acid) | —[b] | 5.2 | 0.1 | 1.3 | x (Minute amount of active ingredient) |
| Comparative Example 5 | Sulfuric acid-impregnated chitin pulverized product (chitin pulverized with addition of acid) | 2.0 | 99 | 10.0 | 60 | Δ (Accumulation of sulfuric acid) |

[a]Substrate/catalyst ratio, i.e., ratio between numbers of moles of NAG monomer unit ($C_8H_{13}NO_5$) and acid catalyst
[b]No catalyst
[c]The solubilization ratio and the total yield of the products are reversed probably because phosphoric acid supported on chitin is not completely removed by washing and the apparent solubilization ratio is reduced.

[Method 2 (Hydrolysis Reaction)]

Examples 3 to 7 and Comparative Example 6

Figure 2:
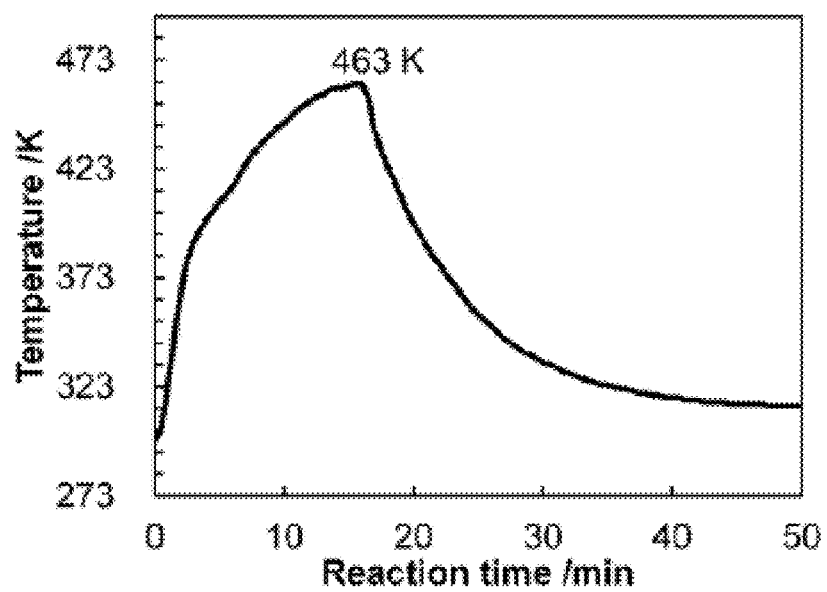
FIG. 2 is a temperature profile of a hydrolysis reaction of a chitin oligomer performed at a reaction temperature of 190° C. (Example 5).

Each sample shown in Table 2 in an amount corresponding to 406 mg in terms of chitin (2 mmol in terms of NAG unit) and 40 mL of water were placed in a high-pressure reactor (internal volume: 100 mL, autoclave manufactured by OM Lab-tech Co., Ltd., made of Hastelloy (trademark) C22), and were then heated from room temperature to a reaction temperature shown in Table 2 for about 16 minutes while being stirred at 600 rpm. At the time point when the reaction temperature was reached, the heating was stopped, and the reactor was air-cooled. After the cooling, the reaction liquid was separated with a centrifuge into a liquid and a solid, and the supernatant sample was analyzed. A temperature profile in the case where the reaction temperature is 190° C. is as shown in FIG. 2.

The product in the liquid-phase sample from which a solid content had been removed was quantitatively analyzed for NAG by HPLC (apparatus: LC-10ATVP manufactured by Shimadzu Corporation, column: Phenomenex Rezex RPM-Monosaccharide Pb++ φ7.8×300 mm, mobile phase: water, 0.6 mL/min, 70° C., and column: Shodex (trademark) SUGAR SH-1011 φ8×300 mm, mobile phase: water, 0.5 mL/min, 50° C., detection: differential refractive index).

An equation for the yield of the product is shown below.

NAG yield (%)={(number of moles of NAG)/(number of moles of NAG unit in added raw material)}×100

The analysis results are shown in Table 2. NAG was hardly produced under the condition that the untreated chitin was subjected to the reaction at 190° C. (Comparative Example 6), whereas the phosphoric acid-impregnated chitin pulverized product 1 having an S/C ratio of 2.0 had NAG yields in the hydrolysis reaction of 26% at 170° C. (Example 3), 36% at 180° C. (Example 4), and 34% at 190° C. (Example 5). In addition, the phosphoric acid-impregnated chitin pulverized product 2 having an S/C ratio of 1.0 had NAG yields of 40% at 170° C. (Example 6) and 44% at 180° C. (Example 7). It was confirmed that the phosphoric acid-impregnated chitin pulverized product 2 had generally higher NAG yields, and both samples achieved the maximum NAG yields at a temperature of 180° C.

TABLE 2

| | Reaction conditions[a] | | Reaction result |
|---|---|---|---|
| No. | Sample | Reaction temperature (° C.) | NAG yield (%)[b] |
| Example 3 | Phosphoric acid-impregnated chitin pulverized product 1 | 170 | 26 |
| Example 4 | Phosphoric acid-impregnated chitin pulverized product 1 | 180 | 36 |
| Example 5 | Phosphoric acid-impregnated chitin pulverized product 1 | 190 | 34 |
| Example 6 | Phosphoric acid-impregnated chitin pulverized product 2 | 170 | 40 |
| Example 7 | Phosphoric acid-impregnated chitin pulverized product 2 | 180 | 44 |
| Comparative Example 6 | Untreated chitin[c] | 190 | ≤1 |

[a]Reaction conditions: chitin: 406 mg, solvent: 40 mL, cooling immediately after heating to reaction temperature
[b]Based on number of moles of NAG monomer unit ($C_8H_{13}NO_5$)
[c]No catalyst

INDUSTRIAL APPLICABILITY

According to the methods of the present invention, the chitin oligomer, N-acetylglucosamine, and the 1-O-alkyl-N-acetylglucosamine can be efficiently produced from chitin with a reduced environmental load and at low cost using a weak acid catalyst that is easy to handle in a use amount of the acid catalyst smaller than in existing production methods, and thus highly functional materials useful in the fields of pharmaceuticals, cosmetics, food, agriculture, and feed can be provided.

The invention claimed is:

1. A method of producing a chitin oligomer, including subjecting chitin-containing biomass to partial hydrolysis while pulverizing the chitin-containing biomass with a pulverization apparatus in the co-presence of water and an acid catalyst selected from phosphoric acid, nitrous acid, and an organic acid,
   wherein a ratio (S/C) of a number of moles (S) of an N-acetylglucosamine unit ($C_8H_{13}NO_5$) in chitin to a number of moles (C) of the acid catalyst is from 1 to 10.

2. The method of producing a chitin oligomer according to claim 1, wherein the acid catalyst is phosphoric acid.

3. The method of producing a chitin oligomer according to claim 1, wherein the pulverizing includes pulverizing the chitin-containing biomass, which is impregnated with the acid catalyst in advance, in the presence of water.

4. The method of producing a chitin oligomer according to claim 3, wherein the method includes mixing a solvent having dissolved therein the acid catalyst with the chitin-containing biomass, then removing the solvent to impregnate the chitin-containing biomass with the acid catalyst, and pulverizing the resultant chitin-containing biomass impregnated with the acid catalyst in the presence of water.

5. The method of producing a chitin oligomer according to claim 4, wherein the solvent is free of modifying the chitin-containing biomass, free of inhibiting acid catalyst activity, and capable of being removed by heating or distillation.

6. The method of producing a chitin oligomer according to claim 5, wherein the solvent is selected from water, diethyl ether, hexane, and benzene.

7. The method of producing a chitin oligomer according to claim 1, wherein the pulverization apparatus is a ball mill.

8. The method of producing a chitin oligomer according to claim 7, wherein the ball mill is a planetary ball mill or a tumbling ball mill.

9. The method of producing a chitin oligomer according to claim 1, wherein the chitin-containing biomass impregnated with the acid catalyst and subjected to the partial hydrolysis has 1 mass % to 3 mass % of water physisorbed thereto.

10. The method of producing a chitin oligomer according to claim 1, wherein the ratio (S/C) is from 1 to 2.

11. A method of producing N-acetylglucosamine, including hydrolyzing a chitin oligomer obtained by the method of claim 1 by adding water thereto, followed by heating.

12. The method of producing N-acetylglucosamine according to claim 11, wherein the heating is performed at a temperature of from 100° C. to 260° C.

13. A method of producing a 1-O-alkyl-N-acetylglucosamine, including alcoholyzing a chitin oligomer obtained by the method of claim 1 by adding an alcohol thereto.

14. The method of producing a 1-O-alkyl-N-acetylglucosamine according to claim 13, wherein the alcohol is a monohydric alcohol.

15. The method of producing a 1-O-alkyl-N-acetylglucosamine according to claim 13, wherein the alcohol is methanol, and wherein the 1-O-alkyl-N-acetylglucosamine is 1-O-methyl-N-acetylglucosamine.

16. The method of producing a 1-O-alkyl-N-acetylglucosamine according to claim 13, wherein the alcoholysis is performed under heating at a temperature of from 120° C. to 280° C.

* * * * *